United States Patent [19]

Hansske et al.

[11] Patent Number: 5,217,990
[45] Date of Patent: Jun. 8, 1993

[54] USE OF MACROLACTONES AS ANTI-ALLERGICS

[75] Inventors: Fritz Hansske, Hirschberg; Otto-Henning Wilhelms, Weinheim-Rittenweimer; Heidrun Anke, Kaiserslautern, all of Fed. Rep. of Germany

[73] Assignee: Boehringer Mannheim GmbH, Mannheim, Fed. Rep. of Germany

[21] Appl. No.: 743,312

[22] PCT Filed: Feb. 16, 1990

[86] PCT No.: PCT/EP90/00251
§ 371 Date: Aug. 19, 1991
§ 102(e) Date: Aug. 19, 1991

[87] PCT Pub. No.: WO90/09790
PCT Pub. Date: Sep. 7, 1990

[30] Foreign Application Priority Data

Feb. 28, 1989 [DE] Fed. Rep. of Germany ....... 3906214

[51] Int. Cl.$^5$ ............................................. A61K 31/365
[52] U.S. Cl. ................................. 514/450; 549/266; 549/271
[58] Field of Search ................. 549/266, 271; 514/450

[56] References Cited
FOREIGN PATENT DOCUMENTS
0133376 2/1985 European Pat. Off. .
0209274 1/1987 European Pat. Off. .

Primary Examiner—C. Warren Ivy
Assistant Examiner—Ba K. Trinh
Attorney, Agent, or Firm—Nikaido, Marmelstein, Murray & Oram

[57] ABSTRACT

The use is described of macrolactones, such as cladospolides and patulolides, as medicaments for the treatment of allergic-inflammatory diseases.

9 Claims, No Drawings

USE OF MACROLACTONES AS ANTI-ALLERGICS

The invention concerns the use of macrolactones of the general formula

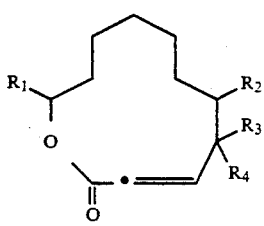

wherein $R_1$ represents a hydrogen atom or a $C_1$–$C_4$-alkyl radical, $R_2$ a hydrogen atom, a hydroxyl or an acetoxy radical, $R_3$, $R_4$, in each case independently of one another, a hydrogen atom, a hydroxyl or an acetoxy radical or together an oxygen atom and —•= a cis- or trans-configurated carbon centre, for the treatment of allergic and inflammatory illnesses, especially for the inhibition of the activation of pro-inflammatory-acting leukocytes, such as e.g. the antigen-induced degranulation of peripheral human leukocytes.

All of the compounds encompassed by the general formula I are known and described or can be prepared in analogous manner from known compounds.

Thus, cladospolides A and B were isolated from Cladosporium cladosporioides (A. Hirota et al., Agric. Biol. Chem., 49 ((1985) 731). The absolute stereo-chemistry on the three asymmetric centres was determined by relevant NMR methods and X-ray structural analyses (H. Hirota et al., Bull. Chem. Soc. Jpn., 58 (1985) 2147; H. Hirota et al., Agric. Biol. Chem., 49((1985) 903). The total synthesis of cladospolide A was recently described (K. Mori et al., Liebigs Ann. Chemie, ((1987) 863).

The diacetates of cladospolides A and B are obtained in per se known manner by acetylation in pyridine with acetic anhydride.

Patulolides A, B and C were isolated from Penicillium urticae mutants S 11 (ATCC 48165) or S 11 R 59 (IFO 31725) (D. Rodphaya et al., J. Antibiotics, 39 (1986) 629; J. Sekiguchi et al., Tetrahedron Letters, 26, (1985)) 2341).

The biosynthesis of these compounds was recently elucidated (D. Rodphaya et al., J. Antibiotics, 41 ((1988) 1649).

The total synthesis were also recently described (K. Mori et al., Liebigs Ann. Chem. ((1988) 13).

The previously known biological activity of the macrolactones according to claim 2 is limited to the following spheres:

Cladospolide A acts weakly inhibitingly on the root growth of lettuce seeds (Lactuca sativa), whereas, in the same test system, cladospolide B acts promotingly (A. Hirota et al., Agric. biol. Chem., 49 ((1985) 731). The hydrogenation products of cladospolides A and B were also described. They possess no biological activity in the above sense (A. Hirota et al., Agric. Biol. Chem., 49 ((1985) 731).

Patulolides A, B and C have also been described as weakly fungistatic and anti-bacterial active materials but also as plant growth inhibiting materials (D. Rodphaya et al., J. Antibiotics, 39 (1986) 629; JP-222192, 4.10.1985, Takeda Chemical Ind. K.K.).

Surprisingly, it could now be found in simple in vitro screening systems that the compounds according to the invention inhibit the activation of leukocytes for mediator liberation and, furthermore, also exhibit a spasm-inhibiting, anti-allergic activity. This action was demonstrated in the test process for anti-allergics, the antigen-caused constriction of passive sensitised guinea pig lung parenchyma strips.

Therefore, the subject of the present invention is the use of macrolactones of the general formula I:

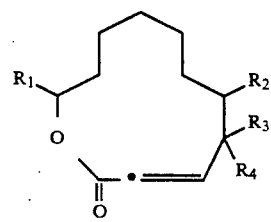

wherein $R_1$ represents a hydrogen atom or a $C_1$–$C_4$-alkyl radical, $R_2$ a hydrogen atom, a hydroxyl or an acetoxy radical, $R_3$, $R_4$, in each case independently of one another, a hydrogen atom, a hydroxyl or an acetoxy radical or together an oxygen atom and —•= a cis- or trans-configurated carbon centre, for the treatment of allergic diseases.

By $C_1$–$C_4$-alkyl therein is understood a methyl, ethyl, propyl or butyl radical, preferably methyl.

Quite especially preferred are the compounds in which $R_1$=methyl and $R_2$=hydrogen and $R_3$ and $R_4$ together represent an oxygen atom; the double bond possesses cis- or trans-substitution.

For the detection of the anti-allergic action, there was used the inhibition of the proteinase liberation from peripheral human leukocytes induced by anti-IgE antibodies (Wilhelmset et al. XII Congress Europ. Acad. Allergology Clin. Immunology, Rome, Sep. 25—3), 1983, as well as DE-Al-34 46 714) or of the histamine liberation in an analogous process according to a further development of the method of R. P. Siraganian and W. A. Hook (Manual of Clinical Immunology, 2nd edition, 1980, pub. N. R. Rose and H. Friedman, Am. Soc. for Microbiology, pages 808 to 821).

Description of the Test System for the Testing for Mediator Liberation Inhibition from Human Leukocytes in Vitro

Principle

The liberation of proteinase on isolated human leukocytes is initiated by stimulation with anti-IgE antibodies (IgE-mediated mediator liberation from basophilic granulocytes). The intensity of this liberation reaction is determined by substrate addition (chromozyme TH) and photometric measurement in that the colour intensity of the samples±inhibitor addition are compared.

Cell Material

Buffy-coat cells=concentrated cell suspension from blood preserve.

In the following Table I are reproduced the inhibition values of the anti-IgE-induced liberation of histamine and proteinase from peripheral human leukocytes. As comparison substance, there was used the known degranulation inhibitor theophylline.

TABLE I

| substance | conc. µg/ml | % inhibition histamine | % inhibition proteinase |
|---|---|---|---|
| cladospolide A | 10 | 44 | 46 |
|  | 2 | 8 | 5 |
| diacetylcladospolide A[+)] | 10 | 92 | 96 |
|  | 2 | 17 | 14 |
| patulolide A | 10 | 100 | 99 |
|  | 2 | 44 | 46 |
| patulolide B | 10 | 100 | 99 |
|  | 2 | 57 | 63 |
| theophylline | 90 | 72 | 70 |

[+)] $R_1$ = ⋯CH₃
$R_2$ = ⋯O Ac
$R_3$ = ⋯O Ac
$R_4$ = ◂H

As further detection for the anti-allergic action, there was investigated the inhibition of the antigen-caused constriction of passive sensitised guinea pig lung parenchyma strips in vitro.

Inhibition of the Antigen-Caused Construction of Passively Sensitised Guinea Pig Lung Parenchyma Strips in Vitro (Organ Bath)

For the in vitro investigation of the compounds according to the invention, there was measured the inhibition of the antigen-caused constriction on passively sensitised guinea pig lung parenchyma strips, as described in the following.

Pirbright white guinea pigs were stunned by neck blow and exsanguinated. The lungs were rinsed in situ substantially free of blood with Krebs buffer, pH 7.4.

Subsequently, the lung was removed, cut up into strips (about 20×4×4 mm) and the strips passively sensitised for 1 hour at room temperature with a 1:50 dilution of a homologous anti-ovalbumin antiserum and then washed with Krebs buffer 1×.

The antiserum had been previously produced in guinea pigs of the same strain according to Davies G. E., T. P. Johnstone (Quantitative studies on anaphylaxis in guinea pigs passively sensitised with homologous antibody; Inter. Arch. 41, 648–654 (1971)) by repeated injection of ovalbumin (2×crystallised) with the addition of complete Freund's adjuvant.

Up to its use, the antiserum was stored undiluted at −18° C.

Subsequently, the lung strips were suspended individually in 10 ml. waterbaths with a prestressing of 1.2 g on an isometric measurement recorder.

Thereafter, the waterbaths were filled with Krebs buffer and continuously gassed at 37° C. with $O_2$ (95%) and $CO_2$ (5%).

The constructions of the lung strips were recorded on a disc via an amplifier.

After 30 minutes acclimatisation phase, histamine control spasms were produced for the recognition of the reaction ability of the organ pieces, washed, subsequently the test substance pre-incubated for 20 minutes at 37° C. and thereafter the ovalbumin-caused constriction initiated.

The inhibition actions of the compounds according to the invention were expressed as percentage reduction of the constriction amplitude of the "samples with test substance" in comparison with the "untreated control constrictions".

The results are given in Table II.

TABLE II

Passively sensitised guinea pig lung parenchyma strips
Inhibition of the antigen-caused constriction by potential mediator liberation inhibitors (organ bath)
Spasmogens and concentrations:

| substance | A | B | C | D | n |
|---|---|---|---|---|---|
| diacetylcladospolide A 40.00 mcg/ml | 6 | 44 | 45 | 46 | 3 |
| patulolide B 40.00 mcg/ml | 3 | 95 | 93 | 93 | 3 |
| patulolide B 10.00 mcg/ml | 5 | 54 | 47 | 51 | 3 |
| cladospolide A 40.00 mcg/ml | 16 | 34 | 33 | 24 | 3 |
| cladospolide A 10.00 mcg/ml | −5 | −50 | −85 | −76 | 1 |
| patulolide A 40.00 mcg/ml | 21 | 51 | 53 | 30 | 3 |
| patulolide A 10.00 mcg/ml | 23 | 35 | 35 | 35 | 1 |
| patulolide C 40.00 mcg/ml | −24 | −40 | −36 | −33 | 3 R |
| patulolide C 10.00 mcg/ml | −38 | −35 | −98 | −26 | 3 |

A = histamine    1.0 [mcg/ml]
B = ovalbumin    0.1 [mcg/ml]
C = glucose      1.16 [%]
D = ovalbumin    1.0 [mcg/ml]
n = number of experiments    R = relaxation The compounds of the general formula I used according to the invention can be used in the usual pharmaceutical compositions and forms of administration especially suitable for anti-allergics, e.g. as tablets, dragees, suppositories, injection solutions, juices, inhalation sprays etc. The medicaments preferably contain the active material together with usual pharmaceutical carrier and dilution agents, possibly also in combination with other active materials, such as e.g. further anti-allergics, or further suitable active materials for the allergy therapy, such as e.g. bronchorelaxants, anti-cholinergics, β-stimulants, mucolytics, anti-inflammatory and fever-lowering-acting agents, vitamins etc. The daily dose administered depends especially upon the nature and severity of the disease; in the case of adult humans, as a rule it amounts to 0.01 to 100 mg of active substance, preferably 0.1 to 10 mg.

EXAMPLE

Diacetylcladospolide A 50 mg (0.22 mmol) cladospolide A are stirred for 16 hrs. at room temperature in 1 ml pyridine with 225 mg (2.2 mmol) acetic anhydride. After standard working up and chromatography on silica gel, 59 mg of chromatographically pure title compound are isolated. Recrystallisation from hexane. M.p. 74° C.

$R_f$ (sil, CHCl₃/MeOH=9:1): 0.34, cladospolide A; 0.68, diacetylcladospolide A.

We claim:

1. A method of treating an allergic condition or an inflammatory disease in a patient in need of such treatment, said method comprising administering to the patient an antiallergic effective amount or an antiinflammatory effective amount of an macrolactone of the formula:

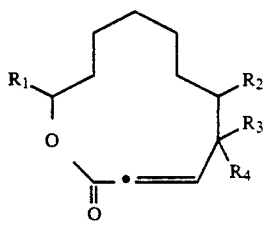

wherein
- $R_1$ is a hydrogen atom or $C_1$–$C_4$-alkyl;
- $R_2$ is a hydrogen atom, a hydroxyl group or an acetoxy radical;
- $R_3$ and $R_4$ are independently a hydrogen atom, a hydroxyl group or an acetoxy radical, or $R_3$ and $R_4$ together are an oxygen atom; and
- —•= is a cis- or trans-configured carbon center.

2. Method of claim 1, wherein the macrolactone is selected from the group consisting of

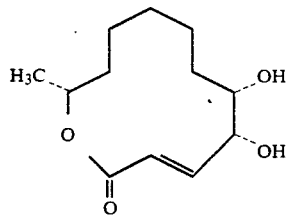

cladospolide A

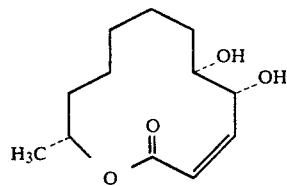

cladospolide B

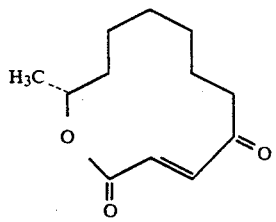

patulolide A and

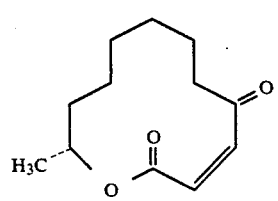

patulolide B

3. Method of claim 1, wherein the treatment is the inhibition of the activation of pro-inflammatory-acting leukocytes.

4. Method of claim 1, wherein the allergic condition is caused by antigen-induced degranulation of peripheral human leukocytes.

5. Pharmaceutical composition suitable for the treatment of allergies comprising an antiallergic-effective amount of a macrolactone of the formula

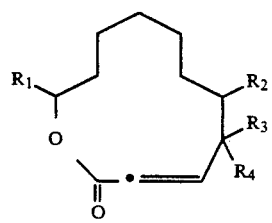

wherein
- $R_1$ is a hydrogen atom or $C_1$–$C_4$-alkyl;
- $R_2$ is a hydrogen atom, a hydroxyl group or an acetoxy radical;
- $R_3$ and $R_4$ are independently a hydrogen atom, a hydroxyl group or an acetoxy radical, or $R_3$ and $R_4$ together are an oxygen atom; and
- —•= is a cis- or trans-configured carbon center, and a pharmaceutically acceptable carrier.

6. Composition of claim 5, wherein the macrolactone is selected from the group consisting of

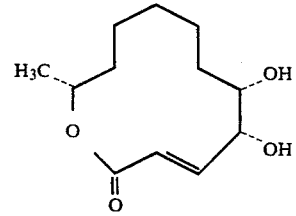

cladospolide A

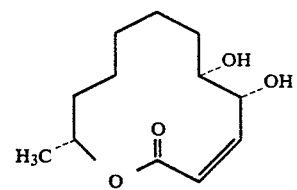

cladospolide B

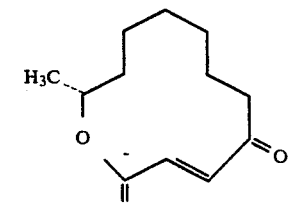

patulolide A and

-continued

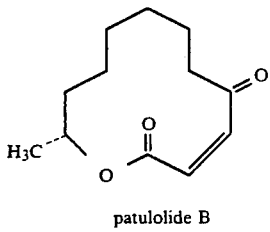

patulolide B

7. A method of treating an allergic condition or an inflammatory disease in a patient in need of such treatment, said method comprising administering to said patient an effective amount of the composition of claim 5.

8. Method of claim 2, wherein the treatment is the inhibition of the activation of pro-inflammatory-acting leukocytes.

9. Method of claim 2, wherein the allergic condition is caused by antigen-induced degranulation of peripheral human leukocytes.

* * * * *